(12) United States Patent
Koyama et al.

(10) Patent No.: US 7,156,091 B2
(45) Date of Patent: Jan. 2, 2007

(54) ORAL AIRWAY AND AIRWAY MANAGEMENT ASSISTIVE DEVICE PROVIDED WITH THE ORAL AIRWAY

(75) Inventors: Junichi Koyama, Nagano (JP); Kei Jin Shu, Tokyo (JP); Takao Nawakura, Tokyo (JP); Yukio Taniguchi, Saitama (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/985,935

(22) Filed: Nov. 12, 2004

(65) Prior Publication Data
US 2005/0150500 A1   Jul. 14, 2005

(30) Foreign Application Priority Data
Nov. 13, 2003   (JP) .............................. 2003-384297

(51) Int. Cl.
*A61M 16/00* (2006.01)
(52) U.S. Cl. .............................. 128/200.26; 128/207.14
(58) Field of Classification Search ........... 128/200.26, 128/207.14, 207.15, 207.16; 600/185, 188, 600/194–199
See application file for complete search history.

(56) References Cited

U.S. PATENT DOCUMENTS

| | | | |
|---|---|---|---|
| 4,067,331 A | | 1/1978 | Berman |
| 4,384,570 A | * | 5/1983 | Roberts ...................... 600/187 |
| 4,527,553 A | | 7/1985 | Upsher |
| 5,203,320 A | | 4/1993 | Augustine |
| 5,381,787 A | * | 1/1995 | Bullard ........................ 600/188 |
| 5,651,761 A | | 7/1997 | Upsher |
| 5,827,178 A | * | 10/1998 | Berall ......................... 600/185 |
| 5,906,578 A | * | 5/1999 | Rajan et al. ................. 600/424 |
| 6,123,666 A | * | 9/2000 | Wrenn et al. ............... 600/188 |
| 6,354,993 B1 | * | 3/2002 | Kaplan et al. .............. 600/188 |
| 6,543,447 B1 | * | 4/2003 | Pacey .................... 128/200.26 |
| 6,676,598 B1 | * | 1/2004 | Rudischhauser et al. ..... 600/188 |
| 6,840,903 B1 | * | 1/2005 | Mazzei et al. .............. 600/188 |
| 6,843,769 B1 | * | 1/2005 | Gandarias ................... 600/189 |
| 6,890,298 B1 | * | 5/2005 | Berci et al. ................. 600/185 |

FOREIGN PATENT DOCUMENTS

| | | |
|---|---|---|
| JP | 8-322937 | 12/1996 |
| WO | 2004/073510 | 9/2004 |

\* cited by examiner

*Primary Examiner*—Teena Mitchell
(74) *Attorney, Agent, or Firm*—Greenblum & Bernstein, P.L.C.

(57) ABSTRACT

An oral airway, which is used by being inserted into the mouth of a patient who is suffering from unconsciousness or has lost consciousness to secure an airway of the patient, is adapted to be used with a tube to be inserted into the trachea of the patient through the mouth thereof. The oral air way includes a main body, and an insertion part provided on the main body. The insertion part is adapted to be inserted into the trachea of the patient through the mouth thereof so that an appropriate portion of the insertion part at the side of the distal end thereof comes into contact with the root of the tongue of the patient to secure the airway of the patient. The insertion part includes a guide groove for guiding the tube when the tube is inserted into the trachea of the patient, and the guide groove has a structure from which the tube can be separated after the distal end of the tube has been inserted into the trachea of the patient.

6 Claims, 3 Drawing Sheets

ORAL AIRWAY AND AIRWAY MANAGEMENT ASSISTIVE DEVICE PROVIDED WITH THE ORAL AIRWAY

BACKGROUND OF THE INVENTION

1. Field of the Invention

The present invention relates to an oral airway for inserting the distal end of a tube of which proximal end is connected to a ventilator into the trachea of a patient, and an airway management assistive device provided with the oral airway.

2. Description of the Prior Art

In a case where a patient is suffering from unconsciousness or has lost consciousness because of an accident or the like, it is sometimes necessary to give rescue breathing as basic life support. Although it is possible to give rescue breathing without using any device, a ventilator is used when necessary. In a case where a ventilator is used, the distal end of a tube of which proximal end is connected to a ventilator is inserted into the trachea of a patient to supply air to the trachea from the ventilator via the tube.

In the meantime, generally, when a person is suffering from unconsciousness or has lost consciousness, the root of the tongue is retracted because of relaxation of the muscles of the pharynx and the larynx and/or loosening of the lower jaw due to the gravity, thereby blocking the airway. Therefore, prior to the insertion of a tube for rescue breathing into the trachea, it is necessary to open such blocked airway to secure the passage of air.

As a device for use in securing the airway, one referred to as an oral airway can be mentioned by way of example. Such an oral airway has an insertion part to be inserted through the mouth of a patient who is suffering from unconsciousness or has lost consciousness. By inserting the insertion part through the mouth of such a patient so that an appropriate portion located on the distal end side of the insertion part can come into contact with the root of the tongue of the patient, it is possible to widen or open the root of the tongue, thereby enabling the airway to be secured. However, since the oral airway is used for only securing the airway, an operator cannot observe a site from the pharynx to the larynx (and the rima glottidis in the larynx) during the use thereof. This means that it is difficult for the operator to insert a tube into the trachea of the patient in a state that such an oral airway is being used, since the operator can not observe the site.

On the other hand, a laryngoscope can also be mentioned as a device having the function of securing the airway. Such a laryngoscope has a bar-like shaped distal end portion for use in securing the airway, image acquiring means provided on the distal end portion, and means for observing an image taken by the image acquiring means. The laryngoscope has both the functions of securing the airway and observing a site from the pharynx to the larynx. The use of such a laryngoscope makes it possible to observe a site from the pharynx to the larynx when an operator inserts a tube into the trachea of a patient. Therefore, insertion of a tube into the trachea can be carried out easily to a certain extent. However, since a tube to be inserted is made of a flexible material and the rima glottidis is narrow, insertion of such a tube through the rima glottidis into the trachea still requires specialized expertise.

As described above, the use of such a conventional device still requires an operator to have specialized expertise for inserting a tube into the trachea of a patient. Other useful devices for use in inserting a tube into the trachea of a patient have also been proposed. However, when using such devices, an operator has to handle a plurality of other devices, which results in complicated operations.

SUMMARY OF THE INVENTION

It is therefore an object of the present invention to provide an oral airway that can insert the distal end of a tube of which proximal end is to be connected to a ventilator into the trachea a patient safely and easily without using any other devices.

In order to achieve the above-mentioned object, the present invention is directed to an oral airway which is used by being inserted into the mouth of a patient who is suffering from unconsciousness or has lost consciousness to secure an airway of the patient, the oral airway being adapted to be used with a tube to be inserted into the trachea of the patient through the mouth thereof. The oral air way includes a main body, and an insertion part provided on the main body and having a distal end. The insertion part is adapted to be inserted into the trachea of the patient through the mouth thereof so that an appropriate portion of the insertion part at the side of the distal end thereof comes into contact with the root of the tongue of the patient to secure the airway of the patient. The insertion part includes guide means for guiding the tube when the tube is inserted into the trachea of the patient, and the guide means has a structure from which the tube can be separated after the distal end of the tube has been inserted into the trachea of the patient.

As described above, the insertion part of the oral airway is provided with the guide means for guiding the tube to be inserted into the trachea of the patient, and the guide means has the structure from which the tube can be separated after the distal end of the tube has been inserted into the trachea of the patient. Namely, the oral airway of the present invention has not only the function of securing the airway of the patient in the same manner as the conventional oral airway but also the function of capable of carrying out an inserting operation of the tube into the trachea easily and safely.

Therefore, according to the oral airway of the present invention, it is possible for an operator to insert the distal end of a tube of which proximal end is connected to a ventilator into the trachea of a patient by itself without using any other devices, and this inserting operation can be carried out easily and safely. Further, since the guide means of the oral airway of the present invention is constructed so that the tube can be separated from the guide means after the distal end of the tube has been inserted into the trachea of the patient. Therefore, according to the present invention, it is possible to remove the oral airway by separating the tube from the oral airway after the tube has been inserted into the trachea of the patient. As a result, since the oral airway of the present invention is used only when it is actually needed for the patient, the burden on the patient can be substantially reduced. In this connection, it is to be noted that the insertion part may be formed into various shapes and formed from various materials so long as it has the function of securing the airway of a patient.

In the present invention, it is preferred that the insertion part further includes illumination means for emitting light; light receiving and image acquiring means for receiving light reflected from the rima glottidis of the patient while the airway is kept open by the insertion part to acquire an image thereof; and image providing means for providing the image formed based on the reflected light to an operator.

According to the oral airway having the above structure, since the operator can insert the distal end of the tube into the rima glottidis which is an entrance to the trachea with monitoring the image of the site displayed on the providing means such as a display device, the tube inserting operation can be carried out more easily.

In this arrangement, the light receiving and image acquiring means and the illumination means are preferably provided on the tip of the insertion part. However, the light receiving and image acquiring means and the illumination means may be provided in the main body. Further, the image providing means may be provided at a position of the oral airway where the operator can see it during use of the oral airway.

Further, in the present invention, it is also preferred that the guide means is formed into a groove having a distal end and provided along the longitudinal direction of the insertion part so that the tube can be guided into the trachea of the patient through the groove.

Furthermore, it is also preferred that the groove is formed with a notch at the distal end thereof so that the tube guided by the groove to the distal end of thereof comes out from the groove with changing its advancing direction toward the notch. By forming such a notch in the groove, the inserting operation of the tube into the trachea becomes easier.

Moreover, it is also preferred that a slanting portion is formed in the groove at a position opposite to the notch so that the distal end of the tube being advanced is directed toward the notch by the slanting portion. This makes it easier to direct the distal end of the tube toward the rima glottides of the patient.

Moreover, in the present invention, it is also preferred that the tube having a circular cross section of a predetermined diameter and made of a flexible material, in which the groove has an opening portion of which width is smaller than the diameter of the tube and the width of the groove is enlarged toward the inside of the groove so that the tube can be separated from the oral airway through the opening portion by deforming the tube in the radial direction thereof.

According to the oral airway having the groove described above, the tube can be guided along the groove with sliding inside the groove along the longitudinal direction thereof. In this case, since the width of the opening portion of the groove is smaller than the diameter of the tube, the tube can be reliably guided within the groove. On the other hand, however, since the tube is formed from a flexible material so as to be deformable, the tube can be separated from the groove by deforming it. Therefore, by pulling the tube out of the groove through the opening portion under the condition that the distal end of the tube is inserted into the trachea of the patient with removing or withdrawing the oral airway from the mouth, it is possible to separate the tube from the groove of the oral airway.

Another aspect of the present invention is directed to an airway management assistive device which comprises: an oral airway which is used by being inserted into the mouth of a patient who is suffering from unconsciousness or has lost consciousness for securing an airway of the patient, the oral airway comprising a main body and an insertion part provided on the main body and having a distal end, the insertion part being adapted to be inserted through the mouth of the patient so that an appropriate portion of the insertion part at the side of the distal end thereof comes into contact with the root of the tongue of the patient to secure the airway of the patient, the insertion part including guide means; and a tube to be guided by the guide means of the oral airway for inserting the distal end of the tube into the trachea of the patient, wherein the guide means having a structure from which the tube can be separated after the distal end of the tube has been inserted into the trachea of the patient.

The airway management assistive device described above is capable of achieving substantially the same operations and results as those of the oral airway of the present invention described above.

These and other objects, structures and results of the present invention will be apparent more clearly when the following detailed description of the preferred embodiments is considered taken in conjunction with the appended drawings.

DETAILED DESCRIPTION OF THE PREFERRED EMBODIMENT

Hereinbelow, a preferred embodiment of the present invention will be described with reference to FIG. 1 to FIG. 5. As will be described later, an oral airway 100 of this embodiment is intended for use with a tube 200 of which distal end is connected to a ventilator, and such an oral airway with the tube is inserted into the trachea of a patient through the mouth thereof. The tube 200 to be used in this embodiment is circular in cross section, and is made of a flexible material such as rubber or the like. In the present invention, a combination of the oral airway 100 and the tube 200 is defined as an airway management assistive device.

Figure 1:
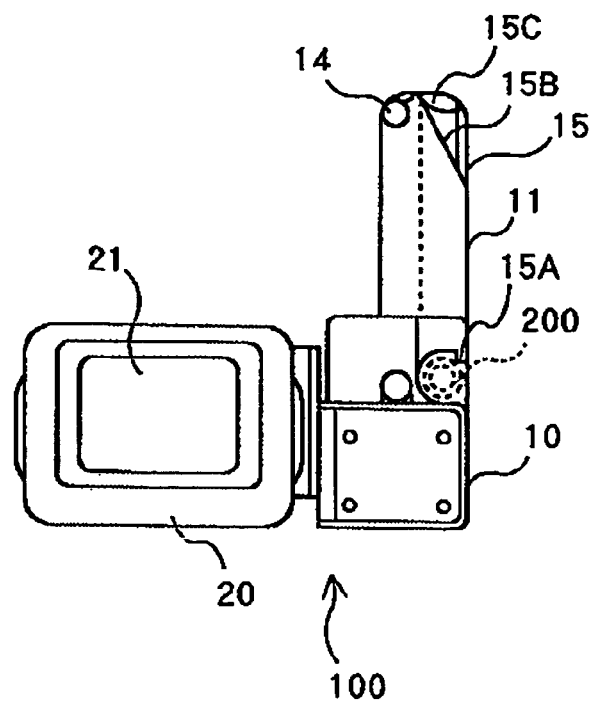
FIG. 1 is a rear view of the oral airway of the present invention.
Figure 2:
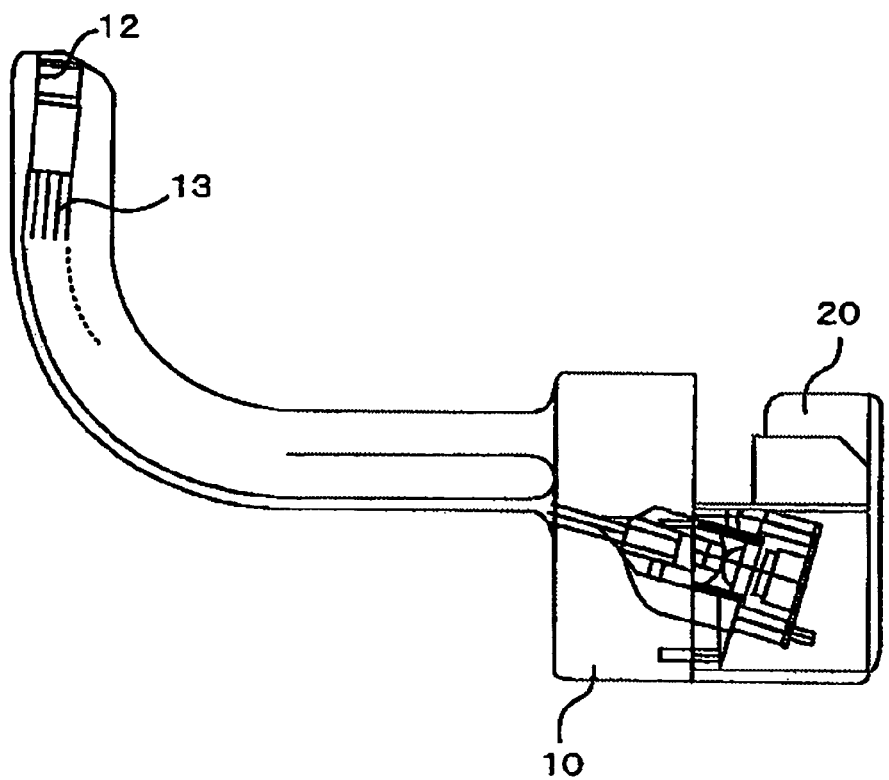
FIG. 2 is a right side view of the oral airway shown in FIG. 1.
Figure 3:
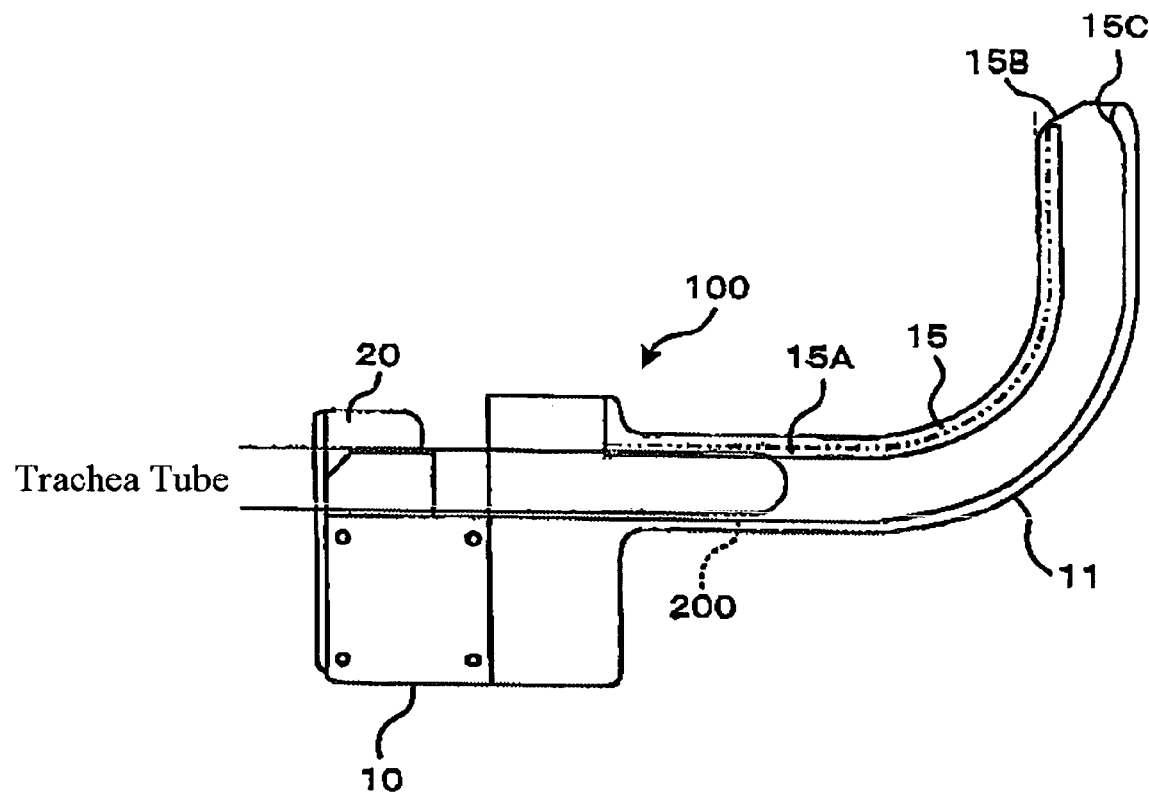
FIG. 3 is a left side view of the oral airway shown in FIG. 1.
Figure 4:
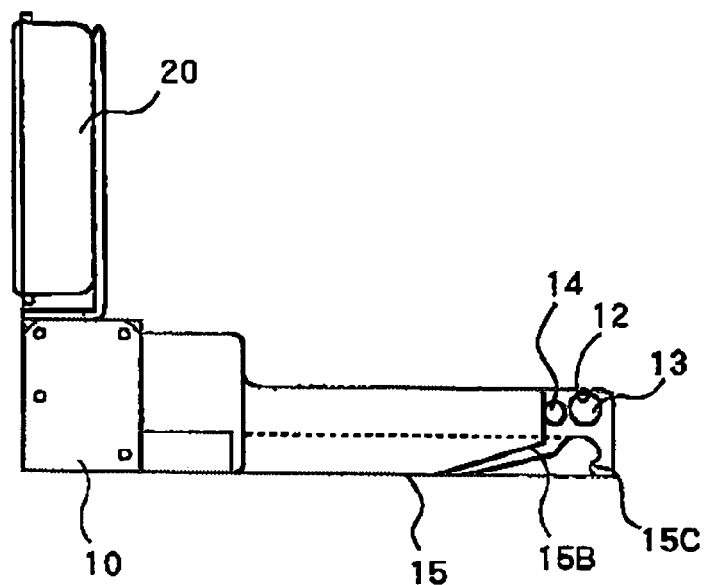
FIG. 4 is a plan view of the oral airway shown in FIG. 1.
Figure 5:
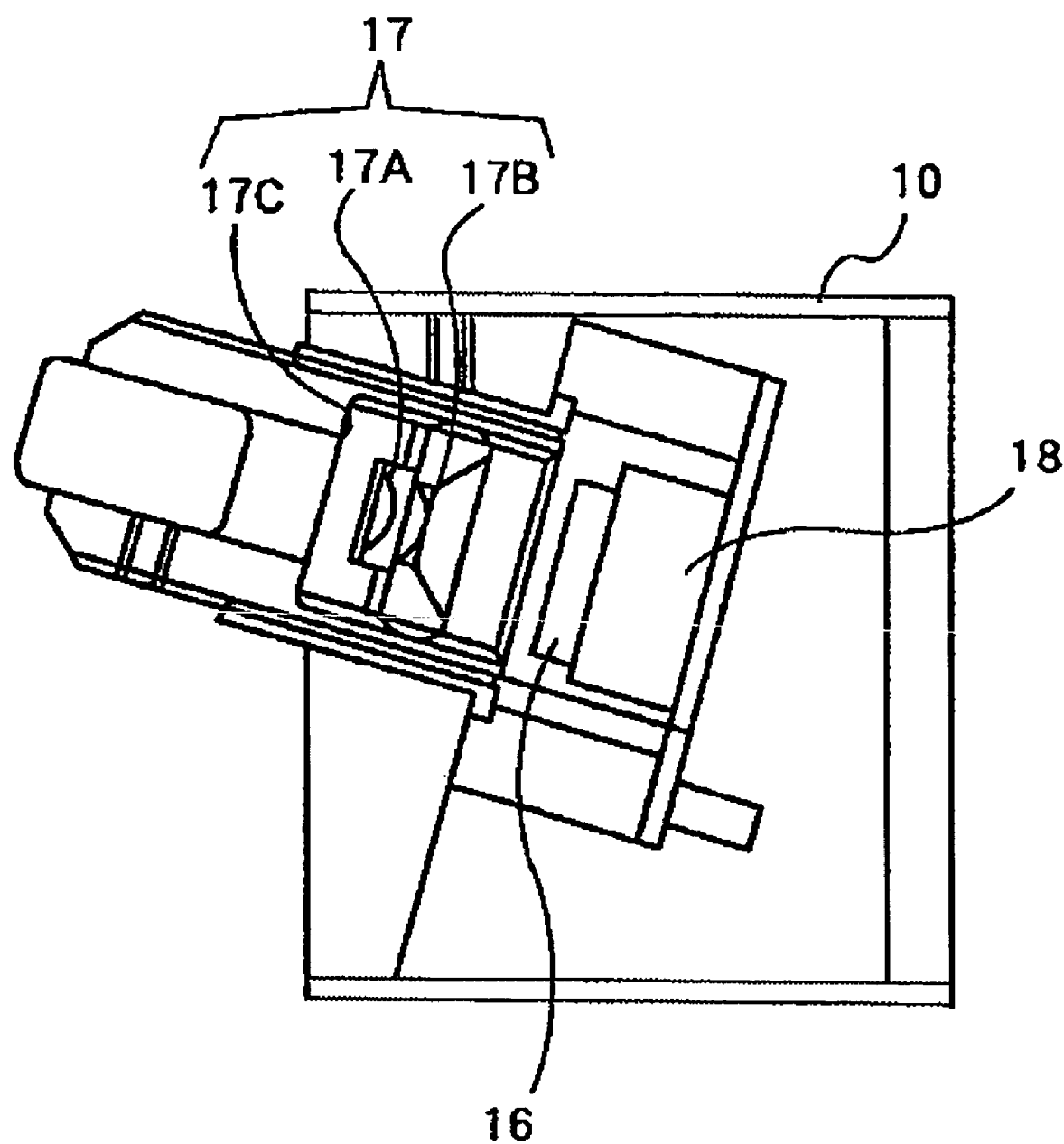
FIG. 5 is an illustration which shows the internal structure of the oral airway shown in FIG. 1.

FIG. 1 is a rear view of the oral airway 100 of the present invention, FIGS. 2 to 4 are a right side view, a left side view, and a plan view of the oral airway 100 shown in FIG. 1, respectively, and FIG. 5 is an illustration which shows the internal structure of the oral airway 100 shown in FIG. 1.

As shown in FIGS. 1 to 4, the oral airway 100 includes a main body 10 and a display device 20 fixed or movably attached to the main body 10.

The main body 10 is provided with an insertion part 11 having the same function as that of an insertion part of an oral airway generally used. The insertion part 11 is a part to be inserted through the mouth of a patient who is suffering from unconsciousness or has lost consciousness. By inserting the insertion part 11 so that an appropriate portion located on the distal end side of the insertion part 11 comes into contact with the root of the tongue of a patient, it is possible to secure the airway of the patient. In the present embodiment, the insertion part 11 is formed into a shape bent at a roughly mid point thereof so that the proximal end and the distal end thereof form an angle of about 90°. It is to be noted that both the insertion part 11 and main body 10 of this embodiment are formed of a resin, and they are integrally formed with each other.

At the distal end of the insertion part 11, there is provided an LED 14 (which acts as "illumination means" of the present invention). The LED 14 is provided to irradiate at least the rima glottidis of a patient with illumination light. In this embodiment, the LED 14 can irradiate the larynx including the rima glottidis of a patient with illumination light. Power is supplied to the LED 14 from a battery (not shown in the drawings) provided in the main body 10 through electric wires (not shown in the drawings) arranged inside the insertion part 11. An operator can turn-on the LED 14 to emit light when necessary by operating a switch not shown in the drawings.

The insertion part 11 has a hollow passage 12 extending from the proximal end to the distal end thereof. The hollow passage 12 is circular in cross section. The hollow passage 12 is opened at the distal end of the insertion part 11. Through the hollow passage 12, an image guide 13 for transmitting light for forming an image extends (which acts as a part of "light receiving and image acquiring means" of the present invention). FIG. 2 shows the oral airway 100 in which the image guide 13 is arranged in the hollow passage 12. The image guide 13 is arranged to receive light emitted by the LED 14 and reflected from an object existing in front of the distal end of the insertion part 11. Specifically, the image guide 13 can receive light emitted by the LED 14 and reflected from at least a site from the larynx to the rima glottidis of a patient while the airway of the patient is kept open by the insertion part 11.

On the left side of the insertion part 11, there is provided a groove 15 extending from the proximal end of the insertion part 11 to the distal end thereof. The groove 15 is provided to guide the tube 200 of which distal end is to be inserted into the trachea of a patient through the mouth thereof, while the airway of the patient is kept open by the insertion part 11. When the tube 200 is inserted into the groove 15, the tube 200 is guided by the groove 15 and is allowed to slide therein toward the rima glottidis back of the larynx while the airway is kept open by the insertion part 11.

In this embodiment, the groove 15 is formed so as to have substantially "U" form in its cross section. Further, in this embodiment, one of the edges of the groove 15 is formed into a rib-shaped stopper 15A along the entire length of the groove 15 to form an opening portion in the form of an elongated slit. The stopper 15A is provided so that the width of the inside portion of the groove 15 is made larger than that of the opening portion (slit) of the groove 15. The width of the opening portion of the groove 15 is made smaller than the diameter (outer diameter) of the tube 200, and the width of a portion on the inner side of the opening portion of the groove 15 is made slightly larger than the diameter (outer diameter) of the tube 200. In this connection, it is to be noted that the stopper 15A may be omitted.

In the distal end portion of the groove 15, a part of an outer wall thereof facing the main body 10 is formed with a notch 15B, and a part of the groove 15 opposite to the outer wall formed with the notch 15B is formed into a slanting surface (convex portion) 15C protruding toward the notch 15B. The slanting surface 15C is designed to come into contact with the tube 200 that has been advanced through the groove 15 so that the advancing direction of the tube 200 is directed toward the notch 15B. This makes it easier to direct the distal end of the tube 200 toward the rima glottides of the patient.

In the oral airway 100 having the above structure, the tube 200 placed inside the groove 15 can be separated from the groove 15 by pulling the tube 200 out of the groove 15 so that the tube 200 is deformed to pass through the opening portion (slit) of the groove 15. Namely, by pulling the tube 200 out of the groove 15 through the opening portion under the condition that the distal end of the tube 200 is inserted into the trachea of the patient while removing or withdrawing the oral airway 100 from the mouth of the patient, it is possible to separate the tube 200 from the groove 15 of the oral airway 10 so that only the tube 200 is being left inside the trachea as it is. As a result, since the oral airway of the present invention is used only when it is actually needed for the patient, the burden on the patient can be substantially reduced.

The main body 10 further includes a CCD 16 (which acts as "light receiving and image acquiring means" of the present invention together with the image guide 13). The CCD 16 is provided so as to be opposite to the proximal end of the image guide 13 in order to form an image based on the light received by the distal end of the image guide 13. That is, an image including the rima glottidis is taken by the CCD 16 based on the light received by the distal end of the image guide 13. It should be noted that the oral airway 100 of this embodiment further includes an optical enlargement system 17 provided between the proximal end of the image guide 13 and the CCD 16. By providing the optical enlargement system 17, it is possible to properly form an enlarged image on the CCD 16 based on the light received by the distal end of the image guide 13. The optical enlargement system 17 of this embodiment includes two magnifiers 17A and 17B and an aperture 17C, but the optical enlargement system is not limited thereto.

The main body 10 further includes a controller 18 for displaying an image on the display device 20 based on image data produced by the CCD 16 from the light received by the distal end of the image guide 13.

Under the control of the controller 18, the display device 20 provides an image based on the image data produced by the CCD 16. The image provided by the display device 20 includes the image of the rima glottidis of a patient while the airway is kept open by the insertion part 11. In this embodiment, the display device 20 has a liquid crystal display 21 as a monitor. On this liquid crystal display 21, the image taken by the CCD 16 is displayed. The display device 20 forms "image providing means" of the present invention.

The oral airway 100 is used in such a manner as described below. Namely, the oral airway 100 is used in a case where it is necessary to insert the tube 200 into the trachea of a patient who is suffering from unconsciousness or has lost consciousness. In this regard, it should be noted that the oral airway 100 is used prior to the insertion of the tube 200 into the trachea of a patient.

First, an operator inserts the insertion part 11 of the oral airway 100 into the mouth of a patient. Specifically, an operator inserts the insertion part 11 into the mouth of the patient so that the inside of a bent portion thereof is fitted to the root of the tongue. In this manner, the insertion part 11 is brought into contact with the root of the tongue, thereby enabling to secure the airway of the patient.

In a state that the airway is being secured, the LED 14 is turned-on to irradiate the airway with illumination light. The distal end of the image guide 13 receives light reflected from the surface of the airway. The light received at the distal end of the image guide 13 is transmitted to the proximal end of the image guide 13, then passed through the optical enlargement system 17, thereby forming an image on the CCD 16. In such a manner, the CCD 16 takes an image of the airway including at least the rima glottidis.

The thus formed image data of the airway including at least the rima glottidis is sent to the display device 20 through the controller 18, and then an image thereof is displayed on the liquid crystal display 21 of the display device 20.

Observing the image on the liquid crystal display 21, the operator inserts the tube 200 into the trachea through the rima glottidis. When inserting the tube 200 into the trachea through the rima glottidis, the operator utilizes the groove 15 of the insertion part 11. As shown in FIG. 1, since the groove 15 is opened at the proximal end of the insertion part 11, the tube 200 is pushed into the groove 15 through the opening. In this way, it is possible to advance the tube 200 through the groove 15 in a sliding manner toward the distal end of the groove 15. When the distal end of the tube 200 reaches the distal end of the groove 15, the distal end of the tube 200 is directed toward the notch 15B by the slanting surface 15C, and then protrudes from the notch 15B (that is, from the distal end of the insertion part 11). At this time, the distal end of the tube 200 is directed to the rima glottides of the patient. Since the notch 15B is provided at such a position as to smoothly lead the curved tube 200 into the rima glottidis, the tube 200 is safely and easily inserted into the trachea. Observing the image (including the image of the distal end of the tube 200) on the display device 20, the operator further inserts the distal end of the tube 200 toward the rima glottidis.

Thereafter, as described above, the tube 200 extending inside the groove 15 can be separated from the groove 15 by pulling the tube 200 out of the groove 15 so that the tube 200 is deformed to pass through the opening portion (slit) of the groove 15. Namely, by pulling the tube 200 out of the groove 15 through the opening portion from the proximal end thereof under the condition that the distal end of the tube 200 is inserted into the trachea of the patient while removing or withdrawing the oral airway 100 from the mouth of the patient, it is possible to separate the tube 200 from the groove 15 of the oral airway 10 so that only the tube 200 is being left inside the trachea as it is. As a result, since the oral airway of the present invention is used only when it is actually needed for the patient, the burden on the patient can be substantially reduced.

Generally, the tube 200 is used with the proximal end thereof being connected to a ventilator. That is, air is supplied to the trachea from a ventilator via the tube 200 that has been inserted into the trachea through the rima glottidis. In this regard, however, it should be noted that the proximal end of the tube 200 is not always connected to a ventilator when the tube 200 is inserted into the trachea.

Finally, it is to be understood that many changes and additions may be made to the embodiment described above without departing from the scope and spirit of the invention as defined in the following claims.

For example, the light receiving means may be constructed from an objective lens and the image providing means may be constructed from an eyepiece lens connected to the objective leans through an optical fiber. Alternatively, the light receiving means may be constructed from an objective lens and a device that can take an image such as a CCD and the image providing means may be constructed from a liquid crystal display electrically connected to the device.

Further, it is also to be understood that the present disclosure relates to subject matter contained in Japanese Patent Application No. 2003-384297 (filed on Nov. 13, 2003) which is expressly incorporated herein by reference in its entirety.

What is claimed is:

1. An oral airway configured to be inserted into the mouth of a patient and to accommodate a tube which is insertable into the trachea of the patient through the mouth of the patient, the oral air way comprising:

a main body; and an insertion part provided on the main body, the insertion part having a distal and a proximal end, wherein the insertion part is configured to be inserted through the mouth of the patient so that a portion around the distal end contacts the root of the tongue of the patient to secure the airway of the patient, the insertion part further including a guide part that guides the tube when the tube is inserted into the trachea of the patient, wherein the guide part includes a groove having a substantially U-shaped cross-section and extending from the proximal end to the distal end of the insertion part such that a continuous opening is provided between the proximal end and the distal end, and the guide part is capable of guiding the tube into the trachea of the patient in a manner such that the tube is capable of being inserted into the groove through the opening and of being completely separated from the insertion part through the opening after the distal end of the tube has been inserted into the trachea of the patient.

2. The oral airway as claimed in claim 1, wherein the insertion part further includes:

an illuminator that emits light;

a light receiver and an image receiver that receives light reflected from the rima glottidis of the patient while the airway is kept open by the insertion part to acquire an image thereof;

and an imager that provides the image formed based on the reflected light to an operator.

3. The oral airway as claimed in claim 1, wherein the groove is formed with a notch at the distal end thereof such that the tube guided by the groove to the distal end of insertion part comes out from the groove changing its advancing direction toward the notch.

4. The oral airway as claimed in claim 3, wherein a slanting portion is formed in the groove at a position opposite to the notch so that the distal end of the tube being advanced is directed toward the notch by the slanting portion.

5. The oral airway as claimed in claim 1, wherein the tube has a circular cross section of a predetermined diameter and is made of a flexible material, wherein the width of the opening of the groove is smaller than the diameter of the tube and the width of the groove is enlarged toward the inside of the groove so that the tube can be separated from the oral airway by deforming the tube in the radial direction thereof.

6. An airway management assistive device, comprising:

an oral airway configured to be inserted into the mouth of a patient, the oral airway comprising a main body and an insertion part provided on the main body and having a distal end, the insertion part being configured to be inserted through the mouth of the patient so that a portion around the distal end thereof contacts the root of the tongue of the patient to secure the airway of the patient, the insertion part further including a guide; and a tube configured to be guided by the guide of the oral airway such that a distal end of the tube is inserted into the trachea of the patient, wherein the guide includes a groove having a substantially U-shaped cross-section and extending from the proximal end to the distal end of the insertion part such that a continuous opening is provided between the proximal end and the distal end, and the guide is capable of guiding the tube into the trachea of the patient in a manner such that the tube is capable of being inserted into the groove through the opening and of being completely separated from the insertion part through the opening after the distal end of the tube has been inserted into the trachea of the patient.

* * * * *